United States Patent [19]

Medcalf, Jr. et al.

[11] Patent Number: 5,064,555

[45] **Date of Patent: * Nov. 12, 1991**

[54] MILD SKIN CLEANSING SOAP BAR WITH HYDRATED CATIONIC POLYMER SKIN CONDITIONER

[75] Inventors: Ralph F. Medcalf, Jr., West Chester; Martha O. Visscher, Cincinnati; John R. Knochel, Cincinnati; Richard M. Dahlgren, Cincinnati, all of Ohio

[73] Assignee: The Procter & Gamble Company, Cincinnati, Ohio

[ * ] Notice: The portion of the term of this patent subsequent to Apr. 11, 2006 has been disclaimed.

[21] Appl. No.: 333,379

[22] Filed: Apr. 5, 1989

Related U.S. Application Data

[63] Continuation of Ser. No. 119,284, Oct. 30, 1987, Pat. No. 4,820,447, which is a continuation of Ser. No. 803,742, Dec. 2, 1985, abandoned.

[51] Int. Cl.[5] ........................ C11D 3/37; C11D 9/30; C11D 17/00

[52] U.S. Cl. .................................... 252/117; 252/121; 252/134; 252/174; 252/174.17; 252/174.23; 252/547; 252/DIG. 16; 252/DIG. 5

[58] Field of Search ............... 252/117, 132, 134, 174, 252/174.17, 547, DIG. 16, DIG. 5

[56] References Cited

U.S. PATENT DOCUMENTS

| | | | |
|---|---|---|---|
| 3,761,464 | 9/1973 | parran, Jr. | 252/106 |
| 4,012,341 | 3/1977 | Orshitzer et al. | 252/548 |
| 4,234,464 | 11/1980 | Morshauser | 252/544 |
| 4,298,494 | 11/1981 | Parslow | 252/174.16 |
| 4,338,211 | 7/1982 | Stiros | 252/142 |
| 4,491,539 | 1/1985 | Hoskins et al. | 252/541 |
| 4,540,507 | 9/1985 | Grollier | 252/174.23 |
| 4,574,053 | 3/1986 | Kinsman et al. | 252/134 |
| 4,820,447 | 4/1989 | Medcalf | 252/117 |

FOREIGN PATENT DOCUMENTS

| | | |
|---|---|---|
| 106193 | 4/1984 | European Pat. Off. . |
| 57-105500 | 6/1982 | Japan . |
| 58-23900 | 10/1983 | Japan . |
| 58-167699 | 10/1983 | Japan . |
| 58-167700 | 10/1983 | Japan . |
| 2094307A | 9/1962 | United Kingdom . |
| 2103236A | 2/1983 | United Kingdom . |

OTHER PUBLICATIONS

"Polymer JR for Skin Care", by Union Carbide, 1977.

Polymers for Personal Care Products, Jaguar C-14-S, Celanese Corp., 3/85.

Polymers for Personal Care Products, Jaguar C-15, Celanese Corp., 4/85.

"The Use of Merquat Polymers in Cosmetics", Sykes et al., Merck & Co., Inc., R-999.1-0, 1978.

*Primary Examiner*—Paul Lieberman

*Assistant Examiner*—Cynthia Leslie

*Attorney, Agent, or Firm*—Leonard Williamson; Robert B. Aylor; Richard C. Witte

[57] ABSTRACT

Disclosed is a mild skin cleansing soap bar composition comprising: (1) 50–90% soap, and (2) a hydrated cationic polymeric skin conditioner. The physical composition of the bar is such that the hydrated polymer is substantially uniformly distributed and well incorporated in the soap. The hydrated cationic polymer improves the mildness of the soap bar to a level approaching that of bars made with very mild synthetic surfactants, while maintaining the desirable physical characteristics of a pure soap bar without the polymer.

The preferred polymer is a hydrated cationic guar gum having a typical aqueous viscosity at 1% of from about 125 cps to about 3500±500 cps.

17 Claims, No Drawings

MILD SKIN CLEANSING SOAP BAR WITH HYDRATED CATIONIC POLYMER SKIN CONDITIONER

CROSS REFERENCE TO RELATED APPLICATIONS

This is a continuation of U.S. Ser. No. 119,284, filed Oct. 30, 1987, now U.S. Pat. No. 4,820,447, issued Apr. 11, 1989, which is a continuation of U.S. Ser. No. 803,742, filed Dec. 2, 1985, now abandoned.

TECHNICAL FIELD

This invention relates to skin cleansing soap bar compositions containing cationic polymers.

BACKGROUND OF THE INVENTION

The cleansing of skin with surface-active cleasning preparations has become a focus of great interest. Many people wash and scrub their skin with various surface-active preparations several times a day. Ideal skin cleansers should cleanse the skin gently, causing little or no irritation, without defatting and overdrying the skin or leaving it taut after frequent routine use. Most lathering soaps, liquids or bars fail in this respect.

As background, reduced skin irritation benefits as measured by patch testing of cationic and nonionic types of polymers are set out in "Polymer JR for Skin Care" Bulletin, by Union Carbide, 1977. The cationic polymers are reported to be preferred over the other polymers because they provide better skin feel benefits.

Attention is directed to J.K.P. No. Sho 58 [1983] 167700, Ohata, et al., which teaches a soap bar with 0.1–6% cationic poly(diethyldiallylammonium chloride) and copolymers thereof. Ohata et al. appears to recognize a problem with the use of other cationic polymers and teach away from the use of the other polymers including JR400.

Attention is directed to U.S. Pat. No. 3,761,418, to Parran, Jr., issued 9/25/73, which discloses detergent compositions containing particle deposition enhancing agents comprising a water-insoluble particulate-cationic polymer mixture. Hydrated cationic guar gum polymers are not mentioned. Parran, Jr.'s Example XV is a 50:50 tallow/coconut (T/CN) fatty acid soap bar which contains 3% cationic polymer. The preparation of the bar, however, is not specified. U.S. Pat. No. 4,012,341, to Orshitzer/Macander, issued 3/15/77, discloses an all-synthetic detergent shampoo bar comprising a mixture of anionic and nonionic detergents. The bars of Examples 2 and 4 contain 1% JR 400. Cationic guar gum polymers are not taught.

U.S. Pat. No. 4,338,211, Stiros, issued July 6, 1982, discloses a liquid skin cleanser with 2.3% to 3% of a synthetic surfactant, polymer JR-400, small amounts of free fatty acid, plus a fatty acid alkylolamide as lather boosting agents.

EPA 106,193, Turney, published 4/25/84, assigned to Union Carbide Corp., teaches liquid skin cleansers with anionic detergent, fatty acid soap and cationic polymer. Soap bars are not taught in either Stiros or Turney.

UK Pat. Appln. GB2094307A, published 9/15/82, assigned to Johnson and Johnson Baby Products Co., discloses amphoteric-fatty acid complexes for detergent products which exhibit good foam and low occular irritancy. This reference teaches that anionic surfactants should not exceed 20% to assure low occular irritancy. Cationic Polymer JR at levels of 0.5 to 3.0% is taught. Liquids and bars are disclosed. Cationic guar gum polymers are not disclosed and skin mildness is not discussed.

Attention is also directed to U.S. Pat. No. 4,234,464, to Morshauser, which issued 11/18/80. This reference discloses a detergent synbar in Example 6 which comprises: 45% isethionate, 5% alkyl amide, 37.5% stearic ($C_{18}$) acid, 5.0% hydrogenated tallow glycerides and 1% Polymer JR. This patent also discloses a wide range of synthetic surfactants and fatty materials. The synbars comprise up to 5% soap "without substantial detriment" and up to 1.5% cationic polymer. Cationic guar gums are not mentioned.

U.S. Pat. No. 4,491,539, James J. Hoskins and Adriaan Kessler, issued Jan. 1, 1985, discloses liquid cleansing products comprising about 5% to 30% of surfactant, about 0.1% to about 1.0% of guar material, about 0.15% to about 1.0% of nonionic carboxyvinyl polymer, and water. Soap bar compositions are not disclosed. Another reference is British Pat. No. 2,103,236A, Colgate, Feb. 16, 1984, which discloses a liquid detergent containing guar gum and a ternary surfactant mixture including a betaine. Soap bar compositions are not disclosed. Also, British Pat. No. 2,114,994A, L'Oreal, Sept. 1, 1983, discloses a cleansing product based on acylisethionates and cationic polymers. These products are not based on soap.

Although it is known that cationic polymers provide hair and skin conditioning properties, none of the above references teach the use of low levels of hydrated cationic guar gum polymers in a soap-based bar. None indicate that the important in-use soap bar characteristics (lather character and volume, rinsing, soap bar feel, etc.) are preserved in the presence of polymers. None indicate that the hydrated cationic guar gum polymers must be well hydrated, incorporated and dispersed in the soap bar in order to achieve improved mildness while maintaining desirable soap bar properties.

It was indeed surprising and unexpected that low levels of hydrated cationic guar gum polymers would provide mildness in a soap-based bar that is nearly equal to synbar products based on mild synthetic surfactants, while maintaining desirable bar soap properties. It was unexpected that the hydration of the cationic guar gum polymers was necessary in order to achieve good incorporation into the soap bar which in turn leads to the mildness and maintenance of soap bar properties.

OBJECTS OF THE INVENTION

This invention relates to skin cleansing toilet bar compositions which provide improved skin mildness. Therefore, one object of this invention is to provide a method of making a skin cleansing toilet bar composition comprising hydrated cationic polymers which exhibit improved skin mildness.

Another object of the present invention is the physical composition of a skin cleansing toilet bar which has improved skin feel and mildness benefits and in which the polymer is well hydrated and uniformly distributed in the soap bar.

Yet another object of the present invention is to provide for more efficient utilization of a cationic skin conditioning agent in soap bars.

Other objects will become apparent from the detailed description below.

SUMMARY OF THE INVENTION

Disclosed is a mild skin cleansing soap bar composition comprising: (1) 50–90% soap, and (2) a hydrated cationic polymeric skin conditioner. The physical composition of the bar is such that the hydrated polymer is substantially uniformly distributed and well incorporated in the soap. The hydrated cationic polymer improves the mildness of the soap bar to a level approaching that of bars made with very mild synthetic surfactants, while maintaining the desirable physical characteristics of soap bars.

DETAILED DESCRIPTION OF THE INVENTION

Disclosed is a mild skin cleansing soap bar composition comprising: (1) 50–90% soap, and (2) a hydrated cationic polymeric skin conditioner. The physical composition of the bar is such that the hydrated polymer is substantially uniformly distributed and well incorporated in the soap. The hydrated cationic polymer improves the mildness of the soap bar to a level approaching that of bars made with very mild synthetic surfactants, while maintaining the desirable physical characteristics of soap bars.

Disclosed is a mild soap bar composition comprising:

(1) 50–90% soap; and (2) an effective amount of a hydrated cationic polymeric skin conditioner uniformly distributed and incorporated in said soap bar, said cationic polymeric skin conditioner having a molecular weight of from 1000 to 3,000,000, said cationic polymeric skin conditioner comprising a skin conditioning amount of a hydrated cationic guar gum having a 1–2% aqueous solution viscosity of from about 125 cps to about 3500±500 cps at 25° C., wherein said aqueous solution has a pH of about 9 to 11, and from 0% to about 5% of another cationic polymeric skin conditioner selected from the group consisting of:

- (I) other cationic polysaccharides;
- (II) cationic copolymers of saccharides and synthetic cationic monomers, and
- (III) synthetic polymers selected from the group consisting of:
  - (A) cationic polyakylene imines,
  - (B) cationic ethoxypolyalkylene imines, and
  - (C) cationic poly(N-(3-(dimethylammonio)propyl)-N'-(3-(ethyleneoxyethylene dimethylammonio)-propyl)urea dichloride); and
- (IV) mixtures thereof; and wherein said bar is substantially free of unhydrated polymeric particles greater than 30 microns; and (3) from about 7% to about 25% moisture.

The soap bar of this invention comprises at least 50% soap as its primary or sole surfactant and also contains as an essential ingredient an effective amount of a "hydrated" cationic polymer which significantly improves the mildness relative to a comparable soap bar without the hydrated polymer. The mildness achieved approaches that of products based on mild synthetic surfactants. Yet the bar maintains the highly acceptable physical and in-use characteristics of a pure soap bar. The polymer is hydrated and uniformly dispersed and incorporated into the soap bar. As used herein the term "cationic polymer" includes naturally and synthetically derived cationic polymers. The abbreviation "CN" means coconut and "T" means tallow herein, unless otherwise specified. All percentages and proportions are by weight, unless otherwise specified.

The soap bar of this invention comprises about 1.2% to 5%, preferably 1.2% to 2%, of a suitably hydrated cationic polymer having a molecular weight of from about 1000 to about 3,000,000, preferably one selected from cationic guar gums having a molecular weight range of 2,500–350,000.

The soap bar of this invention also comprises from about 50% to about 90% soap, preferably at least 25% of tallow soap. The preferred bar of this invention comprises 50–80% T/CN fatty acid soap mixture.

A preferred soap bar of this invention also contains from about 2% to about 17% moisturizer, preferably one selected from glycerin and free fatty acid or mixtures thereof. The more preferred bar of this invention contains at least 4% moisturizer.

In a method of making the bar of the present invention, the cationic polymer is hydrated with water prior to mixing it with the soap during the soap bar making process. Hydration of the polymer produces, with some cationic polymers, a fluid liquid. With other cationic polymers, e.g. cationic guar gum, a rigid gel is produced which can then be reduced to smaller particles. In either case the hydrated polymer incorporates into the soap mix readily and the polymer is distributed uniformly without significant numbers of nonhydrated polymer chunks. The uniform distribution of the polymer maintains highly acceptable soap bar in-use characteristics.

THE SURFACTANT

The fatty acid soaps which are essentials of this invention are alkali metal soaps of fatty acids having alkyl chain lengths of $C_8$–$C_{22}$, preferably $C_{12}$–$C_{18}$, and especially those of the $C_{10}$–$C_{14}$ chain lengths which are important in producing lather rapidly and of good, highly acceptable quality. It is understood that coconut soap is interchangeable with palm kernel oil soap. The fatty acid soaps are present at a level of 50–90%, preferably from 60–80%, and most preferably from 65–70%. The preferred soap has a ratio of tallow/coconut soap of from 0.1:1 to 9:1, preferably from 1:1 to 1.5:1.

The soap bars of this invention can contain up to 20% of a synthetic surfactant. If a synthetic surfactant is included, a mild one is preferred. A mild synthetic surfactant is defined herein as one which does relatively little damage to the barrier function of the stratum corneum. The mild surfactant is present in the present composition at a level of 0–20%, preferably about 2–15%. The fatty acid soap and mild surfactant mixture preferably has a ratio of 2.5:1 to 37:1, preferably from 2.5:1 to 14:1, and most preferably from 6.5:1 to 14:1, soap:synthetic.

Some preferred mild synthetic surfactants useful in this invention include alkyl glyceryl ether sulfonate (AGS), anionic acyl sarcosinates, methyl acyl taurates, N-acyl glutamates, alkyl glucosides, acyl isethionates, alkyl sulfosuccinate, alkyl phosphate esters, ethoxylated alkyl phosphate esters, alkyl ether sulfates, methyl glucose esters, protein condensates, mixtures of alkyl ether sulfates and alkyl amine oxides, betaines, sultaines, and mixtures thereof. Included in the surfactants are the alkyl ether sulfates with 1 to 12 ethoxy groups, especially ammonium and sodium lauryl ether sulfates. Alkyl chain lengths for these surfactants are $C_8$–$C_{22}$, preferably $C_{10}$–$C_{18}$. The most preferred mild surfactant is sodium CN AGS.

MOISTURIZERS/EMOLLIENTS

Moisturizers may be included to provide the skin conditioning benefits and to improve the mildness of the product. The selection of the levels and types of moisturizers to be incorporated into the product is made without adversely affecting the stability of the product or its in-use characteristics, thereby delivering good moisturization and lather.

The term "moisturizer" is often used within the cosmetic industry without very exact definition. The term is sometimes used as synonymous with emollient, and is then meant to describe a material which imparts a smooth and soft feeling to the skin surface.

There are two ways of reducing water loss from the stratum corneum. One is to deposit on the surface of the skin an occlusive layer which reduces the rate of evaporation. The second method is to add nonocclusive hygroscopic substances to the stratum corneum which will retain water, and make this water available to the stratum corneum to alter its physical properties and produce a cosmetically desirable effect. Nonocclusive moisturizers also function by improving the lubricity of the skin.

Both occlusive and nonocclusive moisturizers are suitable for use in the present invention. Some examples of moisturizers are long chain fatty acids, liquid water-soluble polyols, glycerin, propylene glycol, sorbitol, polyethylene glycol, ethoxylated/propoxylated ethers of methyl glucose (e.g., methyl gluceth-20) and ethoxylated/propoxylated ethers of lanolin alcohol (e.g., Solulan-75).

When moisturizers are used in the compositions of the present invention they are used at levels of from about 2% to about 20% by weight of the composition. The preferred and more preferred levels of moisturizers are, respectively, 4% to 15% and 8% to 12%. The preferred moisturizers are the coconut and tallow fatty acids. Some other preferred moisturizers are the nonocclusive liquid water-soluble polyols (e.g., glycerin) and the essential amino acid compounds found naturally in the skin. The most preferred moisturizer is a mixture of coconut fatty acid and glycerin having a ratio of from 2:1 to 0.5:1, coconut fatty acid:glycerin.

The total surfactant (i.e., soap plus any synthetic surfactant, if used) to moisturizer ratio is preferably 4:1 to 39:1 and, more preferably, 9:1 to 20:1, surfactant:moisturizer.

Other preferred nonocclusive moisturizers are compounds found to be naturally occurring in the stratum corneum of the skin, such as sodium pyrrolidone carboxylic acid, lactic acid, urea, L-proline, guanidine and pyrrolidone. Examples of other nonocclusive moisturizers include hexadecyl, myristyl, isodecyl or isopropyl esters of adipic, lactic, oleic, stearic, isostearic, myristic or linoleic acids, as well as many of their corresponding alcohol esters (sodium isostearoyl-2-lactylate, sodium capryl lactylate), hydrolyzed protein and other collagen-derived proteins, aloe vera gel and acetamide MEA (acetmonoethanolamide).

Other examples of both occlusive and nonocclusive types of moisturizers are disclosed in "Emollients—A Critical Evaluation," by J. Mausner, Cosmetics & Toiletries, May 1981, incorporated herein by reference.

THE CATIONIC POLYMER

The cationic polymeric skin conditioning agent essential in the present invention is selected from the group consisting of:

(I) cationic polysaccharides;

(II) cationic copolymers of saccharides and synthetic cationic monomers, and (III) synthetic polymers selected from the group consisting of:

(A) cationic polyakylene imines (B) cationic ethoxy polyalkylene imines, and (C) cationic poly[N-[-3-(dimethylammonio)-propyl]-N'-[3-(ethyleneoxyethylene dimethylammonio)propyl]urea dichloride].

The amount of hydrated cationic polymeric skin conditioners found useful in the composition of the present invention is from about 0.2% to about 5%, preferably from about 0.5% to about 2%, based on the weight of the unhydrated polymer. The bar soap composition containing these relatively small amounts of polymer delivers significantly improved clinical mildness relative to a composition without the polymer. The resultant mildness approaches that of synthetic-based skin cleansing products. (It is known that certain synbars are generally milder than those based on soap, particularly the lower chain length fatty acid soaps.) The mildness improvement is further demonstrated by an improved barrier function of the stratum corneum relative to a product without polymer, as determined by measurement of transepidermal water loss. The cationic polymers used in this invention also provide a desirable silky, soft, smooth in-use feeling. It is believed that the positively charged polymer combines with the negatively charged sites on the skin to provide a soft skin feel after use.

The cationic polymers employed in this invention achieve the mildness benefit while maintaining the highly acceptable and desirable in-use soap bar characteristics of lather character and creaminess, lather volume, rinsing, skin feel, odor, bar feel, etc. This is unexpected since cationic polymers, particularly when used at the higher levels typically necessary for a mildness improvement and when used without the hydration specified by the present invention, have a significant negative impact on in-use characteristics. For example, they can suppress lather volume and alter its character, result in grainy bar texture, result in poor rinsing, and have negative impact on odor.

For the compositions of the present invention, it is important that the cationic polymer be evenly distributed throughout the soap bar. Hydration of the cationic polymer is essential to the achievement of uniform distribution. Some cationic polymers are commercially available in a prehydrated form, while others are commercially available only in their unhydrated form. Uniform distribution of the polymer in the bar enables the polymer to readily deposit on skin to improve clinical mildness. This distribution helps in the maintenance of the highly acceptable soap bar in-use characteristics (skin feel, good lather, bar smoothness and avoidance of bar cracking upon drying out).

(I)

The cationic polysaccharide class encompasses those polymers based on 5 or 6 carbon sugars and derivatives which have been made cationic by engraphing of cationic moieties on the polysaccharide backbone. They may be composed of one type of sugar or of more than one type, i.e. copolymers of the above derivatives and cationic materials. The monomers may be in straight chain or branched chain geometric arrangements. Cationic polysaccharide polymers include the following: cationic celluloses and hydroxyethylcelluloses; cationic starches and hydroxyalkyl starches; cationic polymers based on arabinose monomers such as those which could be dervied from arabinose vegetable gums; cationic polymers derived from xylose polymers found in materials such as wood, straw, cottonseed hulls, and corn cobs; cationic polymers derived from fucose polymers found as a component of cell walls in seaweed; cationic polymers derived from fructose polymers such as Inulin found in certain plants; cationic polymers based on acid-containing sugars such as galacturonic acid and glucuronic acid; cationic polymers based on amine sugars such as galactosamine and glucosamine; cationic polymers based on 5 and 6 membered ring polyalcohols; cationic polymers based on galactose monomers which occur in plant gums and mucilages; cationic polymers based on mannose monomers such as those found in plants, yeasts, and red algae; cationic polymers based on the galactomannan copolymer known as guar gum obtained from the endosperm of the guar bean.

Specific examples of members of the cationic polysaccaride class include the cationic hydroxyethyl cellulose JR 400 made by Union Carbide Corporation; the cationic starches Stalok® 100, 200, 300 and 400 made by Staley, Inc.; the cationic galactomannans based on guar gum of the Galactasol 800 series by Henkel, Inc. and the Jaguar Series by Celanese Corporation.

(II)

The cationic copolymers of saccharides and synthetic cationic monomers useful in the present invention encompass those containing the following saccharides: glucose, galactose, mannose, arabinose, xylose, fucose, fructose, glucosamine, galactosamine, glucuronic acid, galacturonic acid, and 5 or 6 membered ring polyalcohols. Also included are hydroxymethyl, hydroxyethyl and hydroxypropyl derivatives of the above sugars. When saccharides are bonded to each other in the copolymers, they may be bonded via any of several arrangements, such as 1,4-$\alpha$; 1,4-$\beta$; 1,3-$\alpha$; 1,3-$\beta$ and 1,6 linkages. The synthetic cationic monomers for use in these copolymers can include dimethyldiallylammonium chloride, dimethylaminoethylmethyacrylate, diethyldiallylammonium chloride, N,N-diallyl,N-N-dialkyl ammonium halides, and the like. A preferred cationic polymer is Merquat 550 prepared with dimethyldialkylammonium chloride and acrylamide monomers.

Examples of members of the class of copolymers of saccharides and synthetic cationic monomers include those composed of cellulose derivatives (e.g. hydroxyethyl cellulose) and N,N-diallyl,N-N-dialkyl ammonium chloride available from National Starch Corporation under the tradename Celquat.

(III)

The cationic synthetic polymers useful in the present invention are cationic polyalkylene imines, ethoxypolyalklene imines, and poly[N-[3-(dimethylammonio)-propyl]-N'-[3-(ethyleneoxyethylene dimethylammonio)propyl]urea dichloride] the latter of which is available from Miranol Chemical Company, Inc. under the trademark of Miranol A-15, CAS Reg. No. 68555-36-2.

Preferred cationic polymeric skin conditioning agents of the present invention are those cationic polysaccharides of the cationic guar gum class with molecular weights of 1,000 to 3,000,000. More prefered molecular weights are from 2,500 to 350,000. These polymers have a polysaccharide backbone comprised of galactomannan units and a degree of cationic substitution ranging from about 0.04 per anhydroglucose unit to about 0.80 per anhydroglucose unit with the substituent cationic group being the adduct of 2,3-epoxypropyltrimethyl ammonium chloride to the natural polysaccharide backbone. Examples are JAGUAR C-14-S, C-15 and C-17 sold by Celanese Corporation, which trade literature reports have 1% viscosities of from 125 cps to about 3500±500 cps. In order to achieve the benefits described in this invention, the polymer must have characteristics, either structural or physical which allow it to be suitably and fully hydrated and subsequently well incorporated into the soap matrix.

It is noteworthy that the cationic guar gums JAGUAR C-14-S and C-15 are purposely designed by the supplier to hydrate slowly. This slow hydration feature is believed to be necessary for the typical uses of these guar materials in shampoos and conditioners, where premature hydration and subsequent viscosity growth are detrimental to the formulation process.

The cationic guar gum polymers useful in the present invention have been found to be more effective skin conditioners than those cationic polymers based on hydroxyethyl cellulose (e.g., JR-400 commercially available from Union Carbide Corporation) also useful in the present invention and referred to in U.S. Pat. No. 3,761,418, to Parran, Jr., supra, and in UK Pat. Appln. GB2094307A, supra. Solutions of cationic polymers JAGUAR C-14-S and JR-400 and which contained an anionic surfactant (sodium laurate soap) were evaluated. Skin condition was measured via visual evaluations of dryness and redness and via instrumental assessment of skin condition (transepidermal water loss, skin hydration, and sonic attenuation.) Results indicated the cationic guar gum to be about twice as effective as JR-400. Thus, cationic guar gum is a more efficient skin conditioner than a hydroxyethylcellulose-based cationic polymer and is the most preferred type of cationic polymer for use in the present invention.

The usual optionals can be used in the composition of the present invention, e.g., perfumes and electrolytes may be used in formulating the skin cleansing products, generally at a level of about 0.1% to about 2.5% of the composition. Colorants, and also fillers such as talc and clay, may also be used. Preservatives, e.g., EDTA, generally at a level of less than 1% of the composition, may be incorporated in the cleansing products to prevent microbiological growth. Antibacterials can also be incorporated, usually at levels up to 1.5%.

HYDRATION OF THE POLYMER

The hydrated cationic polymer of this invention is a polymer which has absorbed at least a sufficient amount of water so that it can be substantially uniformly distributed into a soap bar. Preferably the amount of water used for hydration should not be in excess of the amount needed to obtain uniform dispersion of the polymer in the soap, since excess water must be removed during the processing of the soap.

In the present invention, the hydrated polymer is substantially uniformly distributed and well-incorporated into the soap bar. The hydrated polymer in a soap bar can be identified by either of the following evaluations.

1. MICROSCOPIC EVALUATION

Hydrated polymers in a soap bar exhibit a characteristic pattern when viewed with a light microscope in the presence of the cationic substantive sulphan blue dye and photographed on color film. That is, the photographs show a uniform coloration of a blue/green hue, due to a polymer/dye complex. The blue/green coloration due to the polymer/dye complex is observed as being uniform in a soap bar sample containing the hydrated polymer. The area of coloration is preferred to be at least 90% of the sample. Within the polymer-containing regions, the intensity of the color can be variable from one location to another. Additionally, there are very few nonhydrated polymer particles in the photographed field of the microscope. The number of particles in a 264 $cm^2$ area of a field of 77× magnification is less than 100, preferably less than 40, and more preferably less than 10. The visible particles in the soap bars of this invention are about 30 microns or smaller.

Procedure for Microscopic Evaluation

The uniformity of the polymer distribution is assessed using a microscopic evaluation of bars which have been treated with a cationic substantive blue dye. The procedure is outlined as follows:

1. A thin section of the bar is cut and it is approximately 2 cm×1.5 cm and 2–3 mm thick.
2. The section is placed on a microscope slide.
3. A small amount of about 0.1% alcohol-based sulphan blue dye solution is applied to the surface of the section for approximately 30 seconds.
4. The excess dye is then washed off with isopropanol and the bar surface gently dried with compressed air.
5. The stained sections are viewed using a light microscope and either overhead lighting, side lighting, or bottom lighting at magnifications generally of 50–500×.
6. The images are recorded in color on photographic film and developed for viewing.
7. The polymer appears as a blue or green color in the photographs. Uniformity of polymer distribution is assessed and the presence of nonhydrated polymer particles is determined.

2. VISUAL TACTILE EVALUATIONS

Hydration of the polymer can be judged during the soap making process by examination of the soap mix after the polymer has been added and mixed for at least 15 minutes (and before the drying step). It is preferred that no lumps of polymer be visible to the eye during this examination. Additionally, the feel of the resultant bars must not be gritty or grainy upon evaluation in water.

The cationic guar gum polymers require a relatively large amount of water for their hydration. The amount of water is believed to be related to molecular weight whereby higher molecular weight polymers require more water. The preferred ratio of water to polymer for JAGUAR C-15 is about 9 parts water to 1 part polymer. For JAGUAR C-14-S, the ratio is about 19 parts water to one part polymer. The amount of water required to hydrate a polymer is determined experimentally and is believed to be a function of polymeric molecular weight. The molecular weight of C-14-S is about 200,000 to 300,000 and the molecular weight of C-15 is lower and thereby requires less water.

Polymer Hydration

The cationic polymer can be hydrated in water prior to its addition to the soap making process or it can be added to the soapmaking process at a point when there is sufficient water present in the process to hydrate the polymer. In summary, the methods of adding the polymer to the soap making process include the following:

(1) the incorporation of a prehydrated cationic polymer into a crutcher mix (typically 25–40% water) which can include other soap bar ingredients;

(2) direct injection mixing of a prehydrated cationic polymer into a liquid soap stream formulation prior to the soap stream entering a dryer;

(3) dry addition of a well-granulated cationic polymer directly to a crutcher mix of soap containing sufficient water to hydrate the polymer; the crutcher mix can include other soap bar ingredients.

(4) prehydration of polymer with an aqueous solution of a synthetic surfactant prior to mixing with soap in the crutcher; and (5) preparing an aqueous slurry of the polymer (i.e. with insufficient water to fully hydrate the polymer) followed by direct injection mixing of the polymer slurry into a liquid soap formulation stream which in turn contains sufficient water to hydrate the polymer, prior to the soap stream entering the dryer.

A nonlimiting example of a method of cationic polymer hydration is illustrated in Example 1.

EXAMPLE 1

1. 100 g JAGUAR C-15 (powder) are quickly added to 900 g of very cold water (ca. 40°–50° F., 4°–10° C.) which is agitated with a turbine blade mixer.
2. The blend is mixed for 10–15 minutes until it becomes very viscous.
3. The mixture is stored at 140° F. (60° C.) for 12–24 hours to further facilitate hydration. (Storage temperatures from about ambient to even higher than 140° F. can be used in this step). At Step (3) this hydrated polymer is a rigid gel.

Process for Making a Mild Cleansing Composition Based on Soap

In general, procedures common to conventional toilet soap bar making are employed. The hydrated polymer is introduced into an aqueous soap mixture prior to vacuum drying. Typically prior to the drying step the soap mix will have a moisture content of 25% to 40%. In the drying step that moisture level is reduced to ca. 7% to 25% preferably 7% to 15%. The following example utilizes polymer incorporation.

EXAMPLE 2

Crutching Step

About 127.6 parts of a mix containing: 29.8% moisture, 52.7% 50/50 tallow/coconut (T/CN) soap, 16.7% CN AGS paste, 3.3% coconut free fatty acid (CNFA), 3.1% glycerin, and 0.2% NaCl are heated to ca. 150°–200° F. (65°–94° C.). About 10.0 parts of the hydrated polymer JAGUAR C-15 made in accordance with the procedure of Example 1 are mixed in.

Vacuum Drying Step

The crutcher mix is vacuum dried at ca. 50 mm Hg absolute pressure to reduce the moisture content of the mix to ca. 10% and to plod this soap into noodles. These noodles are passed through a milling step once.

Amalgamating Step

The once-milled soap noodles are weighed and placed in a batch amalgamator. To about 99.1 parts noodles in the amalgamator are added: 0.20 part $TiO_2$, 1.4 parts perfume, 0.15 part colorant solution, 0.15 part of a solution which contains ca. 40% EDTA. The combined ingredients are mixed thoroughly.

Milling Step

Three-roll soap mills are set up with all rolls at 85°–105° F. (29°–41° C.). The mixture from the amalgamator is passed through the mills several times to obtain a homogeneous mix. This is an intimate mixing step.

Plodding and Stamping Steps

A conventional plodder is set up with the barrel temperature at about 90° F. (32° C.) and the nose temperature at about 110° F. (43° C.). The plodder used is a dual stage twin screw plodder that allows for a vacuum of about 40 to 65 mm Hg between the two stages. The soap log extruded from the plodder is typically round or oblong in cross-section, and is cut into individual plugs. These plugs are then stamped on a conventional soap stamping apparatus to yield the finished toilet soap bar.

The formulation of the finished bar of this example is set out below as Example 2.

EXAMPLES 2–6

| | Example: | | | | |
|---|---|---|---|---|---|
| | 2 | 3 | 4 | 5 | 6 |
| Base Soap (50T/50CN) | 66.3% | 66.9% | 66.9% | 66.9% | 77.9% |
| Alkyl Glyceryl Ether Sulfonate | 10.0 | 10.0 | 10.0 | 10.0 | — |
| Coconut Fatty Acid | 5.6 | 4.0 | 4.0 | 4.0 | 4.0 |
| Water | 10.0 | 10.0 | 10.0 | 10.0 | 10.0 |
| Glycerin | 4.0 | 4.0 | 4.0 | 4.0 | 4.0 |
| NaCl | 1.0 | 1.0 | 1.0 | 1.0 | 1.0 |
| JAGUAR C-15 | 1.0 | 2.0 | 1.0 | 1.0 | 1.0 |
| JR-400 | — | — | 1.0 | — | — |
| Merquat 550 | — | — | — | 1.0 | — |
| Minors (Perfume, Color, etc.) | 2.1 | 2.1 | 2.1 | 2.1 | 2.1 |

The details of the preparation of Example 2 are set out above. Examples 3–6 are all prepared similar to Example 2, but for the ingredient differences set out in the above table. In Examples 4 and 5, other cationic polymer, JR-400 and Merquat 550 are respectively added in addition to the cationic guar gum JAGUAR C-15. Prehydrated polymers which are not too viscous, e.g., Merquat 550, can be added either in the crutcher or in the amalgamator, as long as uniform distribution is achieved. It should be noted that the JAGUAR C-15 in Example 6 is about 1.2% of polymer based on the weight of the solid soap.

A bar made in accordance with the procedure of Example 2 was examined under magnification in accordance with the dye test previously described herein, and was found to have uniform polymeric distribution with very few remaining discrete particles of nonhydrated cationic guar gum or other cationic polymer.

Other bars were made in accordance with the procedure set out in Example 2 except that unhydrated C-14-S cationic guar gum was added at the amalgamation step. They were observed to be nonuniform and contained a number of large chunks of polymers, which were as large as 120 microns.

Clinical Assessment of the Toilet Bars

The clinical test procedure used to evaluate several toilet bar formulations for skin mildness is given below.

Clinical Mildness Arm Wash Test Procedure

(4 Washes Per Day for Two Weeks for 40 Washes)

The washings were performed by the panelists. Each panelist was assigned a set of two test products for washings. These bars were all kept (in plastic dishes) under technical personnel control. The test procedure for each arm is:

1. Pick up and wet a Masslin towel.
2. Pick up and wet the bar.
3. Rub the bar on the towel for 6 seconds.
4. Put bar aside and rub the towel on the inner forearm from wrist area up to elbow and back down again. Repeat up-down cycle for 10 seconds.
5. Allow lather to remain on for forearm for 90 seconds.
6. Rinse thoroughly for 15 seconds with warm water.
7. Pat dry with paper towel.
8. Wait 5 minutes.
9. Repeat Steps 1–7 above.
10. Return 3–4 hours later to repeat Steps 1–9 above.

Test Product Formulations

The formulations of the products tested clinically are given in Table 1. Composition X is a soap-based control product without polymer. Composition Y is a control product based on synthetic surfactants. Composition B corresponds to Example 2 above. Composition "A" was made in accordance with the procedure set out in Example 2 like Composition "B", but a different cationic guar gum polymer was used and 19 parts of water per 1 part of polymer was required. Composition "X" is a control soap bar without polymer, and Composition "Y" is believed to be the composition of DOVE ®, a prior art benchmark for toilet bar mildness.

TABLE 1

| | Test Product Formulations | | | |
|---|---|---|---|---|
| Composition | X | Y | A | B |
| Na Soap 50/50 T/CN | 67.3% | — | 66.3 | 66.3 |
| $H_2O$ | 10.0 | 7.0 | 10.0 | 10.0 |
| Glycerin | 4.0 | — | 4.0 | 4.0 |
| Free CN Fatty Acid | 5.6 | 2.5 | 5.6 | 5.6 |
| Na $C_{12}$ AGS | 10.0 | — | 10.0 | 10.0 |
| NaCl | 1.0 | 1.35 | 1.0 | 1.0 |
| Minors (Perfume, Color, etc.) | 2.1 | 1.45 | 2.1 | 2.1 |
| Na Soap 85/15 T/CN | — | 11.7 | — | — |
| Na CN Igepon | — | 44.0 | — | — |
| Stearic Acid | — | 26.0 | — | — |
| Na $C_{12}$ Alkyl Benzene Sulfonate | — | 1.8 | — | — |
| Na Stearate | — | 2.4 | — | — |
| Na Isethionate | — | 2.6 | — | — |
| JAGUAR C-14-S | — | — | 1.0 | — |
| JAGUAR C-15 | — | — | — | 1.0 |

Clinical Test Skin Grading Scales

The forearm skin grading scales reported herein are set out below.

Forearm Grading Scale

Skin Dryness

0—Perfect skin.

1.0—Patches of checking and/or slight powderiness and occasional patches of small scales may be seen. Distribution generalized.

2.0—Generalized slight powderiness. Early cracking or occasional small lifting scales may be present.

3.0—Generalized moderate powderiness and/or moderate cracking and lifting scales.

4.0—Generalized heavy powderiness and/or heavy cracking and lifting scales.

5.0—Generalized high cracking and lifting scales. Eczematous change may be present. Powderiness may be present but not prominent. May see bleeding crack.

6.0—Generalized severe cracking. Eczematous change may be present. Bleeding cracks may be present. Scales large, may be beginning to disappear.

Forearm Grading Scales

| Skin Erythema | | Skin Smoothness | |
|---|---|---|---|
| 0 | No redness | 0 | Very high smoothness/slick |
| 1.0 | Barely detectible redness | 1.0 | Extreme smoothness |
| 2.0 | Slight redness | 2.0 | Substantial smoothness |
| 3.0 | Moderate redness | 3.0 | Moderate smoothness |
| 4.0 | Heavy or substantial redness | 4.0 | Slight smoothness |
| 5.0 | Severe redness | 5.0 | Barely detectible smoothness |
| 6.0 | Extreme redness | 6.0 | No smoothness |

The term "generalized" as used herein means that more than 50% of the surface area of the forearm exhibits the attribute. Whole unit skin grades reflect generalized condition. Half units are used to represent intermediate conditions.

Clinical Test Results

The clinical mildness test results expressed in terms of skin grades for dryness, erythema, and smoothness are shown below in Table 2. Example X is a control product without polymer. Example Y is a control product based on a mild, commercially available synbar, DOVE®.

TABLE 2

| | Paired Comparison Skin Grades | | | | | |
|---|---|---|---|---|---|---|
| | One Week | | | Two weeks | | |
| Example | Smoothness | Erythema | Dryness | Smoothness | Erythema | Dryness |
| Y | 1.82 | 1.98 | 2.00 | 3.02 | 3.28 | 3.30 |
| X | 1.98 | 2.42 | 2.40 | 3.20 | 3.66 | 3.70 |
| Difference (Y − X) | −0.16** | −0.44* | −0.40* | −0.18 | −0.38* | −0.40* |
| B | 1.92 | 2.21 | 2.52 | 2.91 | 3.28 | 3.31 |
| X | 2.08 | 2.58 | 2.79 | 3.24 | 3.65 | 3.65 |
| Difference (B − X) | −0.15** | −0.36* | −0.27* | −0.33* | −0.37* | −0.33* |
| A | 2.10 | 2.38 | 2.25 | 2.90 | 3.17 | 3.29 |
| X | 2.23 | 2.33 | 2.15 | 3.35 | 3.44 | 3.58 |
| Difference (A − X) | −0.13** | 0.058 | 0.10 | −0.44* | 0.27* | −0.29* |

*Significant difference at 95% or greater confidence level.
Difference: "+" (second treatment better) "−" (first treatment better)
**Significant difference at 89-94% confidence level.

For smoothness, erythema and dryness, lower numbers indicate better skin condition (see the grading scale set out above). Specifically, in Table 2, for the pair represented by Examples B and X, Example B of this invention has a dryness grade of 3.31, which is lower than the dryness grade of 3.65 for Example X. See Table 1 for the formulations. The difference is calculated as dryness of B minus dryness of X and is −0.33. Therefore, a negative number indicates that the first treatment is better.

TABLE 3

| Single Product Skin Grades | |
|---|---|
| Grade* | Product (vs. Test Product Code) |
| Dryness | |
| 2.98 | Example X (Soap Control) |
| 2.61 | Example B (1% C-15) |
| 2.52 | Example Y (DOVE ®) |
| 2.52 | Example A (1% C-14-S) |
| Grade | Product (vs. Test Product Code) |
| Erythema | |
| 3.20 | Example X |
| 2.87 | Example B |
| 2.78 | Example Y |
| 2.56 | Example A |
| Smoothness | |
| 1.85 | Example X |
| 1.72 | Example Y |
| 1.54 | Example B |
| 1.38 | Example A |

*Reported as change from initial condition.

These Paired Comparative data of Table 2 show that the skin cleansing compositions of this invention (Examples A and B) result in significantly improved mildness over control soap Example X without any polymer in terms of dryness, erythema and smoothness as shown by the above lower grades. See the grading scales set out above. It should be noted that relatively low levels of polymer, 1%, achieved these results. In addition, the Single Product analysis of Table 3 indicates that Example A of this invention is directionally better than Example Y based on mild surfactants. Example B approaches this synbar for mildness also.

What is claimed is:

1. A mild soap bar composition comprising:

(1) 50–90% soap; and (2) and effective amount of a hydrated cationic polymeric skin conditioner uniformly distributed and incorporated in said soap bar, said cationic polymeric skin conditioner having a molecular weight of from 1000 to 3,000,000, said cationic polymeric skin conditioner comprising from about 0.2% to about 5% of a hydrated cationic guar gum having a 1–2% aqueous solution viscosity of from about 125 cps to about 3500±500 cps at 25° C., wherein said aqueous solution has a pH of about 9 to 11, and from 0% to about 5% of another cationic polymeric skin conditioner selected from the group consisting of:

(I) other cationic polysaccharides;

(II) cationic copolymers of saccharides and synthetic cationic monomers, and (III) synthetic polymers selected from the group consisting of:

(A) cationic polyakylene imines, (B) cationic ethoxypolyalkylene imines, and (C) cationic poly(N-(3-(dimethylammonio)propyl)-N'-(3-(ethyleneoxyethylene dimethylammonio)-propyl)urea dichloride); and (IV) mixtures thereof; and wherein said bar is substantially free of unhydrated polymeric particles greater than 30 microns; and (3) from about 7% to about 25% moisture.

2. The mild soap bar composition of claim 1 wherein said composition comprises: from about 50% to about 80% of surface active agent selected from soaps and mixtures of soap and synthetic surfactants wherein said soap is present at a level of at least 50% and said synthetic surfactant can be present up to a level of 20% by weight of said composition; and from about 0% to about 20% of a moisturizer.

3. The mild soap bar composition of claim 1 wherein said soap comprises fatty acid soaps having fatty acid carbon chain lengths of $C_8$–$C_{22}$.

4. The mild soap bar composition of claim 1 wherein said bar contains at least 25% tallow soap.

5. The mild soap bar composition of claim 1 wherein said soap is a mixture of tallow and coconut soaps having a ratio of 0.1:1 to 9:1.

6. The mild soap bar composition of claim 5 wherein said ratio is 1:1 to 1.5:1.

7. The mild soap bar composition of claim 1 wherein said composition contains from about 2% to about 20% of a synthetic surfactant selected from alkyl glyceryl ether sulfonates, anionic acyl sarcosinates, methyl acyl taurates, N-acyl glutamates, alkyl glucosides, acyl isethionates, alkyl sulfosuccinates, alkyl phosphate esters, ethoxylated alkyl phosphate esters, methyl glucose esters, protein condensates, mixtures of ethoxylated alkyl sulfates and alkyl amine oxides, betaines, sultaines, the alkyl ether sulfates with 1 to 12 ethoxy groups, and mixtures thereof, wherein said synthetic surfactants contain $C_8$–$C_{22}$ alkyl chains.

8. The mild soap bar composition of claim 7 wherein said synthetic surfactant has an alkyl chain length of $C_{10}$–$C_{18}$.

9. The mild soap bar composition of claim 1 wherein said composition contains up to 20% of a $C_{10}$–$C_{18}$ alkyl glyceryl ether sulfonate.

10. The mild soap bar composition of claim 1 wherein said composition contains from about 2% to about 17% moisturizer.

11. The mild soap bar composition of claim 1 wherein the other cationic polysaccharide polymer is cationic hydroxyethylcellulose polymer.

12. A method of making a mild soap bar in accordance with claim 1 comprising the steps of:

(1) hydrating an effective amount of said cationic guar gum polymer with water, and (2) uniformly distributing and incorporating the hydrated cationic guar gum polymer into an aqueous soap mix whereby said hydrated cationic guar gum polymer is substantially uniformly distributed and incorporated in said aqueous soap mix, and (3) drying said uniform mix to a moisture level of from 7% to 25%, and (4) forming the dried product obtained by step (3) into a bar shape.

13. The method of making a mild soap bar in accordance with claim 12 wherein said cationic polymer is hydrated in a soap making crutcher step.

14. The method of claim 12 wherein said polymer is hydrated with water prior to mixing with said aqueous soap mix.

15. The method of claim 12 wherein said hydrated polymer is a free flowing liquid and is injected into a liquid soap stream prior to drying.

16. The method of claim 12 wherein said hydrated polymer is a cationic guar gum gel which is mixed in a soap crutcher step mixture containing 25% to 40% water.

17. The method of claim 12 wherein said bar has a moisture level of 7% to 15%.

* * * * *